(12) United States Patent
Kim (10) Patent No.: US 8,805,572 B2
(45) Date of Patent: Aug. 12, 2014

(54) DISPENSARY MANAGEMENT SYSTEM AND METHOD

(75) Inventor: Jun-Ho Kim, Daegu (KR)

(73) Assignee: JVM Co., Ltd. (KR)

( * ) Notice: Subject to any disclaimer, the term of this patent is extended or adjusted under 35 U.S.C. 154(b) by 727 days.

(21) Appl. No.: 12/961,912

(22) Filed: Dec. 7, 2010

(65) Prior Publication Data

US 2011/0160896 A1    Jun. 30, 2011

(30) Foreign Application Priority Data

Dec. 24, 2009  (KR) .......................... 10-2009-0130893

(51) Int. Cl.
*G06F 17/30*   (2006.01)

(52) U.S. Cl.
USPC ............. 700/214; 700/237; 700/231; 702/55; 702/2; 53/154

(58) Field of Classification Search
USPC ......................................................... 700/214
See application file for complete search history.

(56) References Cited

U.S. PATENT DOCUMENTS

| | | | |
|---|---|---|---|
| 6,101,452 A * | 8/2000 | Krall et al. ....................... 702/55 |
| 2005/0212656 A1* | 9/2005 | Denison et al. .............. 340/5.73 |
| 2007/0208595 A1* | 9/2007 | Ohmura et al. .................... 705/2 |
| 2008/0065264 A1* | 3/2008 | Omura et al. ................ 700/231 |
| 2008/0077274 A1* | 3/2008 | Kim .............................. 700/237 |
| 2008/0115456 A1* | 5/2008 | Kim ................................ 53/154 |
| 2011/0120316 A1* | 5/2011 | Castellani et al. .............. 99/280 |

* cited by examiner

*Primary Examiner* — Gene Crawford
*Assistant Examiner* — Kyle Logan
(74) *Attorney, Agent, or Firm* — Cantor Colburn LLP (57) ABSTRACT

A dispensary management system includes a medicine compounding management unit for managing medicine compounding information and for automatically compounding medicines according to the medicine compounding information and a medicine storage management unit connected to the medicine compounding management for storing residual medicines and, when medicines in the medicine compounding management unit are insufficient, for informing the medicine compounding management unit of a position where medicines corresponding to insufficient medicines are stored. A dispensary management method includes inputting medicine compounding information, determining whether medicines are insufficient based on the medicine compounding information, retrieving a cabinet storing medicines corresponding to the insufficient medicines, filling the insufficient medicines, and compounding medicines according to the medicine compounding information.

7 Claims, 10 Drawing Sheets

DISPENSARY MANAGEMENT SYSTEM AND METHOD

BACKGROUND OF THE INVENTION

1. Field of the Invention

The present invention relates to a system for managing and compounding medicines, and, more particularly, to a dispensary management system and method that is capable of independently managing medicine compounding information or medicine information to improve rapidity in medicine compounding based on the medicine compounding information and, when medicines are insufficient during medicine compounding, rapidly retrieving a storage position where medicines corresponding to the insufficient medicines to fill the insufficient medicines.

2. Description of the Related Art

If a large amount of medicines is manually compound in a hospital or a large-scale dispensary where a plurality of kinds of medicines is managed and a large amount of medicines is compound, compounding time is increased, and many errors may occur. In addition, health of patients may be harmed according to circumstances.

Various systems that are capable of retrieving medicines according to medicine compounding information and dispensing medicines according to dosage of the medicines have been developed in order to solve the above problems, Automation of medicine compounding reduces waiting time of patients, personnel expenses, and medication errors due to mistakes of medicine compounding.

In conventional automation systems of medicine compounding, however, a database server for managing the positions of medicines and quantity of stock is included in a medicine compounding management server, with the result that, upon simultaneous retrieval of a plurality of pieces of medicine information, the total flow of a dispensary management system becomes slow, and all medicine compounding processes are paralyzed when the medicine compounding management server is abnormally operated.

Also, measures for insufficient medicines are not sufficiently provided, with the result that it is difficult to perform a prompt notification related to the insufficient medicines, and, upon filling of the insufficient medicines, it is difficult to retrieve the position where medicines corresponding to the insufficient medicines are stored, with the result that medicine filling time is increased.

In addition, a function to store a record related to the filling of medicines, which is performed by a person in charge, is not provided, with the result that efficiency in objective and systematic dispensary management is lowered.

SUMMARY OF THE INVENTION

Therefore, the present invention has been made in view of the above problems.

In one aspect of the present invention, it is an object of the present invention to provide a dispensary management system wherein a database server for managing medicine compounding information or medicine information is independently provided to rapidly achieve a medicine compounding operation based on the medicine compounding information and to rapidly retrieve the storage position of medicines corresponding to insufficient medicines and filling the insufficient medicines during medicine compounding, thereby improving efficiency in operation of the dispensary management system.

It is another object of the present invention to provide a dispensary management system wherein a cabinet management server is included to synthetically manage information on cabinets storing medicines.

It is another object of the present invention to provide a dispensary management system wherein a master cabinet for managing a plurality of cabinets is included to form a systematic management structure.

It is another object of the present invention to provide a dispensary management system wherein a display unit is further included to easily recognize the position of medicine cassettes stored in the cabinet.

It is another object of the present invention to provide a dispensary management system wherein a user authentication unit is further included to confirm information on a user who retrieves medicines and stores and delivers the medicine cassettes.

It is another object of the present invention to provide a dispensary management system wherein each of the medicine cassettes is provided with an identification member, thereby achieving rapidity and accuracy in storage and delivery of the medicine cassettes and in retrieval of position information.

It is a further object of the present invention to provide a dispensary management system that is capable of performing information exchange using a local area network, thereby achieving simplicity of facilities and rapid medicine compounding and medicine retrieval.

In another aspect of the present invention, it is an object of the present invention to provide a dispensary management method that is capable of rapidly retrieving the storage position of medicines corresponding to insufficient medicines during medicine compounding, thereby reducing medicine compounding time and efficiently managing a stock of medicines.

It is another object of the present invention to provide a dispensary management method wherein a user authentication step is included to confirm information on a user who inputs medicine compounding and a user who fills medicines.

It is another object of the present invention to provide a dispensary management method wherein a standby mode step is further included to determine whether a medicine compounding apparatus is normally operating.

It is another object of the present invention to provide a dispensary management method that is capable of accurately confirming a cabinet containing medicines corresponding to the insufficient medicines and position information on medicine cassettes in the cabinet.

It is another object of the present invention to provide a dispensary management method wherein a step of displaying a medicine compounding state and error information is further included to rapidly notify the outside of the medicine compounding state and the error information.

It is another object of the present invention to provide a dispensary management method that is capable of rapidly retrieving information on a cabinet storing medicine cassettes based on medicine information.

It is another object of the present invention to provide a dispensary management method wherein a step of registering identification information on the medicine cassettes and medicine information in advance is included to accurately retrieve the storage position of the medicines and the medicine information.

It is another object of the present invention to provide a dispensary management method that is capable of arranging information on the medicine cassettes based on the available period, thereby improving efficiency in stock management of stored medicines.

It is another object of the present invention to provide a dispensary management method wherein a user authentication step is further included to confirm information on a user who retrieves the medicine cassettes.

It is a further object of the present invention to provide a dispensary management method that is capable of arranging information on the medicine cassettes based on the position of a user, thereby minimizing the length of the line of flow of the user.

In accordance with one aspect of the present invention, the above and other objects can be accomplished by the provision of a dispensary management system including a medicine compounding management unit for managing medicine compounding information and for automatically compounding medicines according to the medicine compounding information and a medicine storage management unit connected to the medicine compounding management for storing residual medicines and, when medicines in the medicine compounding management unit are insufficient, for informing the medicine compounding management unit of a position where medicines corresponding to insufficient medicines are stored.

In accordance with another aspect of the present invention, there is provided a dispensary management method including inputting medicine compounding information, determining whether medicines are insufficient based on the medicine compounding information, retrieving a cabinet storing medicines corresponding to the insufficient medicines, filling the insufficient medicines, and compounding medicines according to the medicine compounding information.

In accordance with a further aspect of the present invention, there is provided a method of retrieving stored medicines, the method including inputting medicine compounding information or medicine information, retrieving a medicine cassette corresponding to the medicine compounding information or medicine information, selecting the retrieved medicine cassette, and storing the selected medicine cassette.

In the dispensary management system according to the present invention, as described above, a database server for managing medicine compounding information or medicine information is independently provided to rapidly achieve a medicine compounding operation based on the medicine compounding information and to rapidly retrieve the storage position of medicines corresponding to insufficient medicines and filling the insufficient medicines during medicine compounding. Consequently, the present invention has the effect of improving efficiency in operation of the dispensary management system.

Also, a database server interconnecting a medicine compounding information and an automatic medicine compounding apparatus is included to improve efficiency in data communication based on the medicine compounding and the retrieval of the insufficient medicines. Consequently, the present invention has the effect of reducing medicine compounding time and retrieval time.

Also, a cabinet management server is included to synthetically manage information on cabinets storing medicines.

Also, a master cabinet for managing a plurality of cabinets is included to form a systematic management structure.

Also, a display unit is further included to easily recognize the position of medicine cassettes stored in the cabinet.

Also, a user authentication unit is further included to confirm information on a user who retrieves medicines and stores and delivers the medicine cassettes.

Also, each of the medicine cassettes is provided with an identification member, thereby achieving rapidity and accuracy in storage and delivery of the medicine cassettes and in retrieval of position information.

Also, the dispensary management system is capable of performing information exchange using a local area network, thereby achieving simplicity of facilities and rapid medicine compounding and medicine retrieval.

In the dispensary management method according to the present invention, as described above, it is possible to rapidly retrieve the storage position of medicines corresponding to insufficient medicines during medicine compounding. Consequently, the present invention has the effect of reducing medicine compounding time and efficiently managing a stock of medicines.

Also, a user authentication step is included to confirm information on a user who inputs medicine compounding and a user who fills medicines.

Also, a standby mode step is further included to determine whether a medicine compounding apparatus is normally operating.

Also, it is possible to accurately confirm a cabinet containing medicines corresponding to the insufficient medicines and position information on medicine cassettes in the cabinet. Consequently, the present invention has the effect of reducing medicine filling time.

Also, a step of displaying a medicine compounding state and error information is further included to rapidly notify the outside of the medicine compounding state and the error information.

Also, it is possible to rapidly retrieve information on a cabinet storing medicine cassettes based on medicine information, thereby rapidly retrieving the storage position of the medicine cassettes.

Also, a step of registering identification information on the medicine cassettes and medicine information in advance is included to accurately retrieve the storage position of the medicines and the medicine information.

Also, it is possible to arrange information on the medicine cassettes based on the available period, thereby improving efficiency in stock management of stored medicines.

Also, a user authentication step is further included to confirm information on a user who retrieves the medicine cassettes, thereby improving accuracy in medicine storage management.

Also, it is possible to arrange information on the medicine cassettes based on the position of a user, thereby minimizing the length of the moving line of the user.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Now, preferred embodiments of the present invention will be described in detail with reference to the accompanying drawings.

Figure 1:
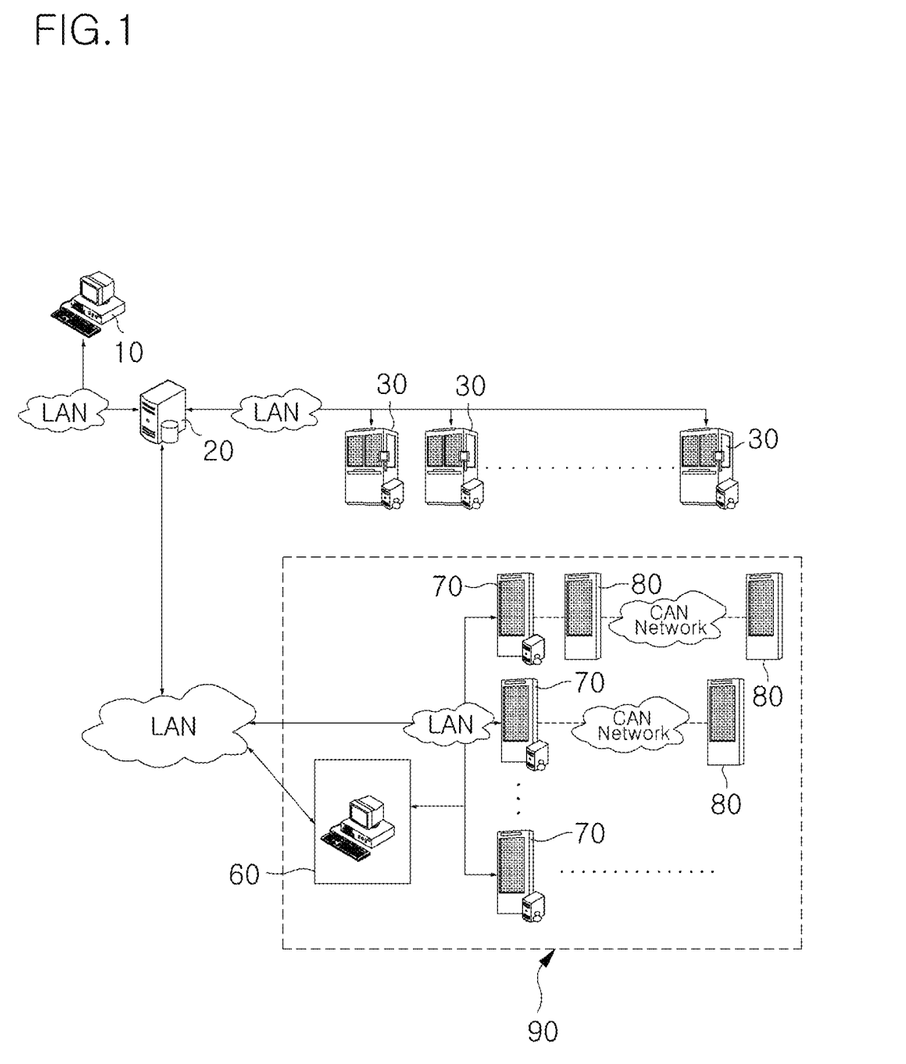
FIG. 1 is an overall construction view of a dispensary management system according to the present invention.

FIG. 1 is a construction view illustrating a dispensary management system according to the present invention. The dispensary management system includes a medicine compounding information server 10, a database server 20, an automatic medicine compounding apparatus 30, and a medicine storage unit 80.

The medicine compounding information server 10 serves to receive and manage medicine information. Also, the medicine compounding information server 10 transmits patient information as well as the received medicine information to the database server 20.

The database server 20 serves to store and manage medicine compounding information including the medicine information and the patient information. Also, the database server 20 transmits the medicine compounding information to the automatic medicine compounding apparatus 30.

In addition, the database server 20 serves to manage medicine information stored for medicine compounding.

The automatic medicine compounding apparatus 30 is connected to the database server 20 for performing an automatic medicine compounding operation according to the medicine compounding information and for determining whether medicines are insufficient. A plurality of automatic medicine compounding apparatuses 30 may be provided according to the scale of a dispensary.

That is, the automatic medicine compounding apparatus 30 immediately determines whether medicines are insufficient, thereby smoothly achieving the medicine compounding operation.

As described above, the database server 20, which stores and manages the medicine compounding information and the medicine information, is independently provided to transmit the medicine compounding information from the medicine compounding information server 10 to the automatic medicine compounding apparatus 30 such that the automatic medicine compounding apparatus 30 can use the medicine compounding information, thereby improving efficiency and rapidity of the medicine compounding operation.

According to the present invention, the medicine compounding information server 10, the database server 20, and the automatic medicine compounding apparatus 30 exchange data with each other via a local area network (LAN).

That is, a medicine compounding management unit constituted by the above components of the dispensary management system is operated through the LAN, thereby achieving facility simplification, rapid medicine compounding, and rapid medicine retrieval.

The medicine storage unit 80 is connected to the medicine compounding management unit for storing residual medicines and for informing the medicine compounding management unit of positions where the medicines are stored when the medicines are insufficient in the medicine compounding management unit. The medicine storage unit 80 includes at least one medicine storage cabinet and a cabinet management server 60 for managing the medicine storage cabinet.

The medicine storage cabinet serves to store a plurality of medicine cassettes containing classified medicines. The medicine storage cabinet includes a master cabinet 70 and a sub cabinet 80.

The sub cabinet 80 serves to store the medicine cassettes in a stacked state.

According to the present invention, each of the medicine cassettes is a storage container for storing medicines to be supplied to the automatic medicine compounding apparatus 30. The medicine cassettes are delivered to the automatic medicine compounding apparatus 30 such that the automatic medicine compounding apparatus 30 can be refilled with medicines contained in the respective medicine cassettes.

Also, according to the present invention, each of the medicine cassettes preferably further includes an individual identification member.

The identification member includes information (medicine names, the dates of manufacture, the available periods, etc.) on medicines stored in each of the medicine cassettes. Information on the storage position of each of the medicine cassettes is stored in the identification member such that the information on the storage position of each of the medicine cassettes can be easily identified through the identification member. In this embodiment of the present invention, a bar code is used as the identification member, to which, however, the present invention is not limited. For example, the identification member may be embodied in various forms.

The masker cabinet 70 further includes a retrieval unit 74 for retrieving information from the sub cabinet 80. The masker cabinet 70 serves to manage information on at least one sub cabinet 80.

That is, as the number of the sub cabinets 80 is increased, time necessary to retrieve insufficient medicines from the automatic medicine compounding apparatus 30 is increased, with the result that it is difficult to manage information on medicines stored in each of the sub cabinets 80 in a batch manner.

In order to solve the above-mentioned problem, the master cabinet 70 is provided to manage at least one sub cabinet 80. Preferably, a plurality of master cabinets 70 is provided such that the sub cabinets 80 are sorted into a plurality of groups based on the number and position of the sub cabinets 80 and each of the master cabinets 70 manages each group of the sub cabinets 80.

It is possible to rapidly retrieve information on medicines in the respective sub cabinets 80 and to systematically manage the sub cabinets 80 by provision of the master cabinet 70.

Figure 2:
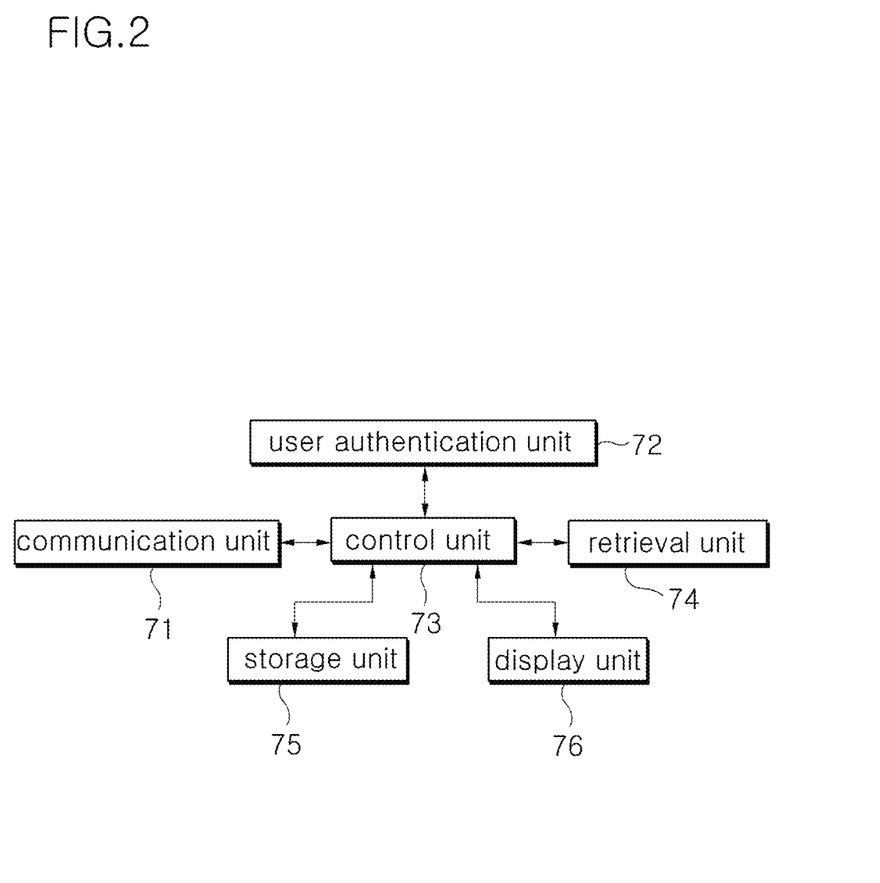
FIG. 2 is a construction view of a master cabinet of the dispensary management system according to the present invention.

FIG. 2 is a detailed construction view of the master cabinet 70. The master cabinet 70 includes a communication unit 71, a user authentication unit 72, a control unit 73, an information retrieval unit 74, a storage unit 75, and a display unit 76.

The communication unit 71 exchanges medicine information data with the sub cabinet 80 linked to the master cabinet 70. Also, the communication unit 71 performs data communication with the cabinet management server 60, which manages the master cabinet 70. The information received by the communication unit 71 is transmitted to the control unit 73.

The information retrieval unit 74 is connected to the control unit 73 for retrieving position information on insufficient medicines through the storage unit 75, which stores information on medicines stored in the sub cabinet 80 linked to the master cabinet 70. Also, the information retrieval unit 74 serves to transmit the retrieved results to the control unit 73.

The display unit 76 serves to display the position information on the medicines retrieved by the information retrieval unit 74. In this embodiment of the present invention, the display unit 76 is embodied as an electric bulletin board configured in a dot matrix structure based on the arrangement of the medicine cassettes.

The user authentication unit 72 serves to authenticate information on a user who retrieves the positions of medicines and stores and delivers the medicine cassettes.

That is, it is possible to improve efficiency in management of a medicine storage management unit 90 constituted the above components of the dispensary management system through the user authentication unit 72.

When the dispensary management system with the above-stated construction according to the present invention is applied, it is possible to rapidly retrieve storage positions of insufficient medicines during automatic medicine compounding based on medicine compounding information, thereby rapidly and smoothly refilling the insufficient medicines and thus improving efficiency in use of the dispensary management system.

Hereinafter, a dispensary management method using the dispensary management system with the above-stated construction according to the present invention will be described in detail.

Figure 3:
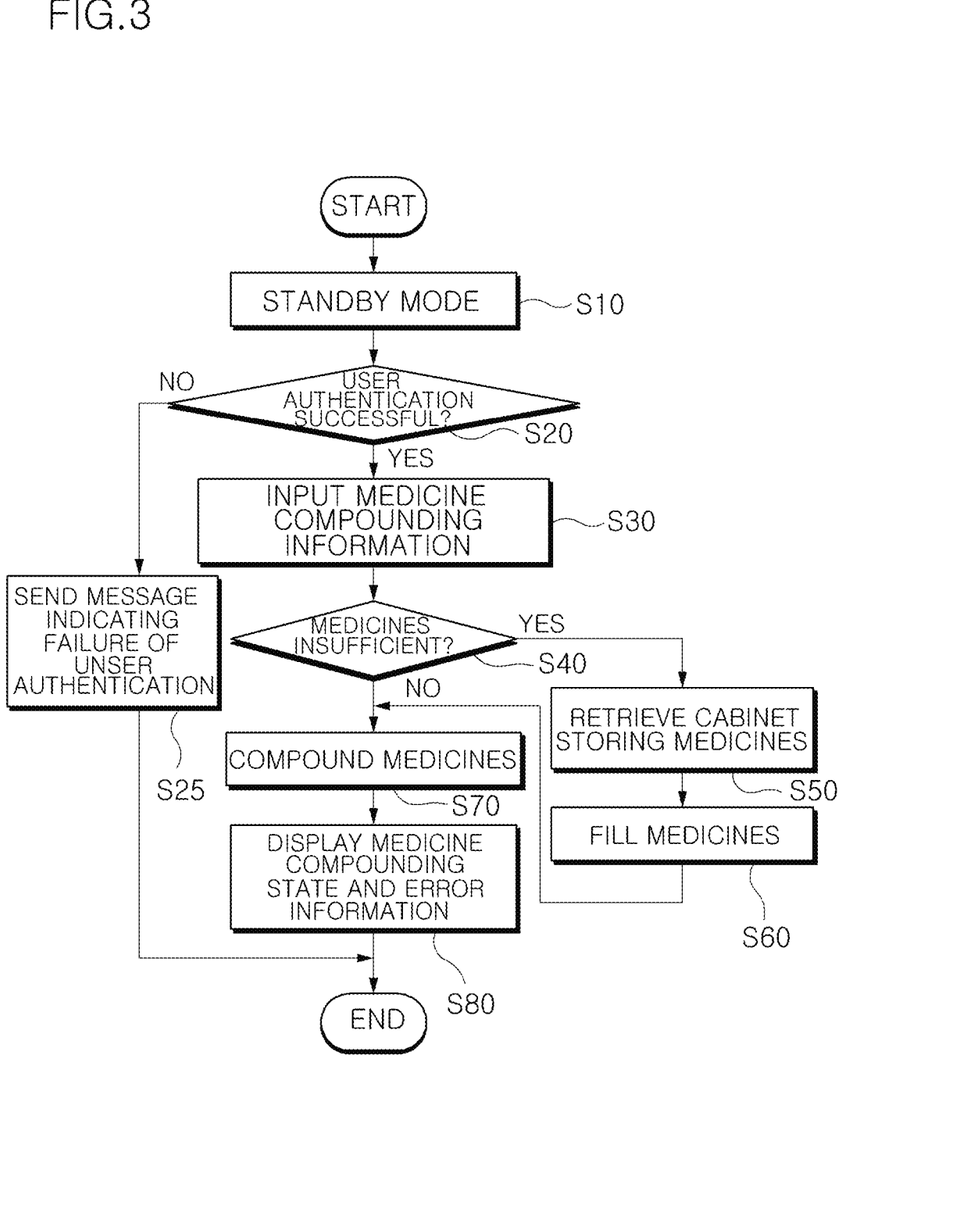
FIG. 3 is an overall flow chart illustrating a dispensary management method according to the present invention.

First, a standby mode step is performed with respect to the medicine compounding information server 10, the database server 20, and the automatic medicine compounding apparatus 30 (S10).

Step S10 is a monitoring step of determining whether the medicine compounding information server 10, the database server 20, and the automatic medicine compounding apparatus 30 are normally operating. It is possible to determine whether the medicine compounding information server 10, the database server 20, and the automatic medicine compounding apparatus 30 are normally operating through Step S10.

Figure 8:
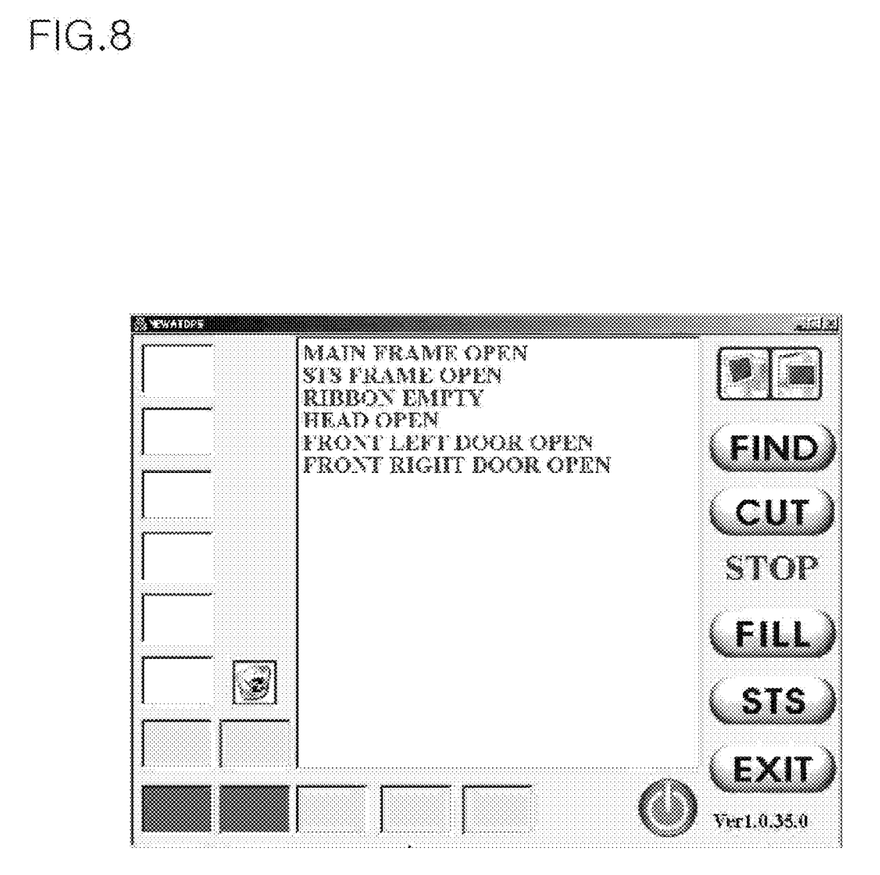
FIG. 8 is a view illustrating an embodiment of Step S10 of the dispensary management method according to the present invention.

FIG. 8 is a view illustrating an embodiment of Step S10 as described above. It is possible to determine whether various sensors of the automatic medicine compounding apparatus 30 are normally operating and whether medicine inlet and outlet ports are open.

Subsequently, a step of determining whether user authentication has been successful is performed (S20).

Step S20 is a step of authenticating information on a user who inputs medicine compounding information. Afterwards, the user information may be used to confirm a person in charge who inputs medicine compounding information.

If it is determined at Step S20 that the user authentication has failed, a step of sending a message indicating failure of the user authentication is performed (S25).

Subsequently, a step of inputting medicine compounding information is performed (S30).

Step S30 is a step of inputting names of medicines to be compounded, quantity of the medicines, and patient information.

Subsequently, a step of determining whether medicines in the automatic medicine compounding apparatus 30 are insufficient is performed (S40).

At Step S40, the quantity of medicines stored in the automatic medicine compounding apparatus 30 is compared with the quantity of medicines based on the medicine compounding information, and, if it is determined that the quantity of medicines stored in the automatic medicine compounding apparatus 30 is less than the quantity of medicines based on the medicine compounding information, the outside is notified of the fact that the medicines in the automatic medicine compounding apparatus 30 are insufficient.

Figure 9:
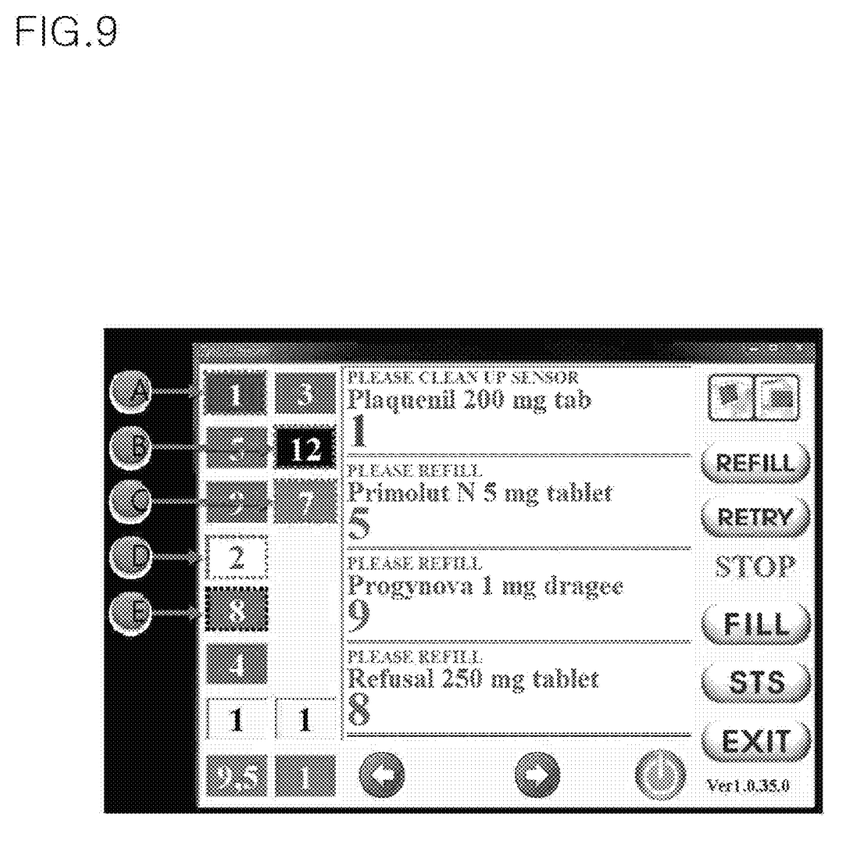
FIG. 9 is a view illustrating an embodiment of Step S40 of the dispensary management method according to the present invention.

FIG. 9 is a view illustrating an embodiment of Step S40 of the dispensary management method according to the present invention. Specifically, FIG. 9 shows a state of the medicine cassettes based on the medicine compounding.

In this embodiment of the present invention, it is indicated that it is necessary to clean a first cassette shown in a green color on a screen (A), medicines in third, fourth, fifth, eighth, and ninth cassettes shown in a red color on the screen are insufficient (E), medicines in a seventh cassette shown in a blue color on the screen are caught by a sensor (C), a twelfth cassette shown in a black color on the screen has no medicine cassette response (B), and medicine distribution from a second medicine cassette shown in a white color on the screen has been completed (D).

If it is determined at Step S40 that the medicines are not insufficient, a step of immediately compounding the medicines is performed (S70).

If it is determined at Step S40 that the medicines are not insufficient, on the other hand, a step of retrieving the cabinet, which stores medicines, using the database server 20 is performed (S50).

Figure 10:
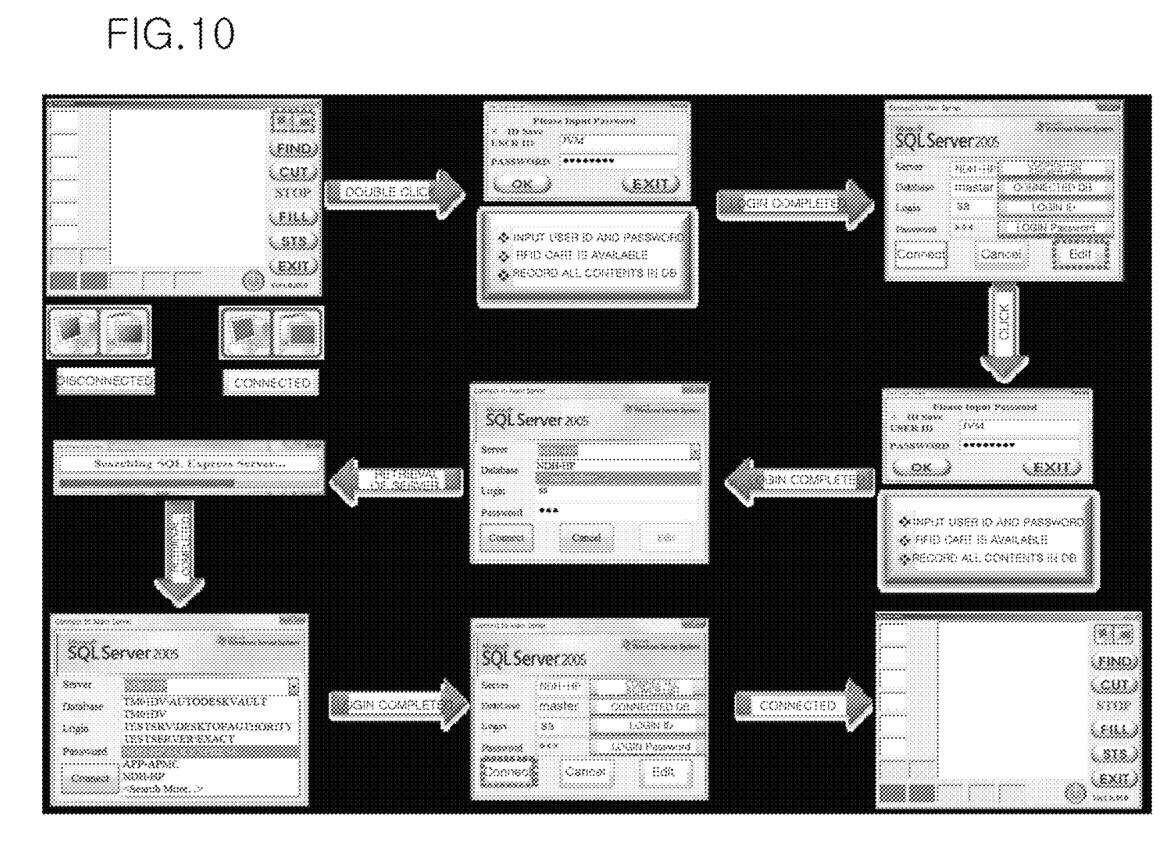
FIG. 10 is a view illustrating an embodiment of Step S50 of the dispensary management method according to the present invention.

FIG. 10 is a view illustrating an embodiment of access to the database server 20 at Step S50.

Figure 4:
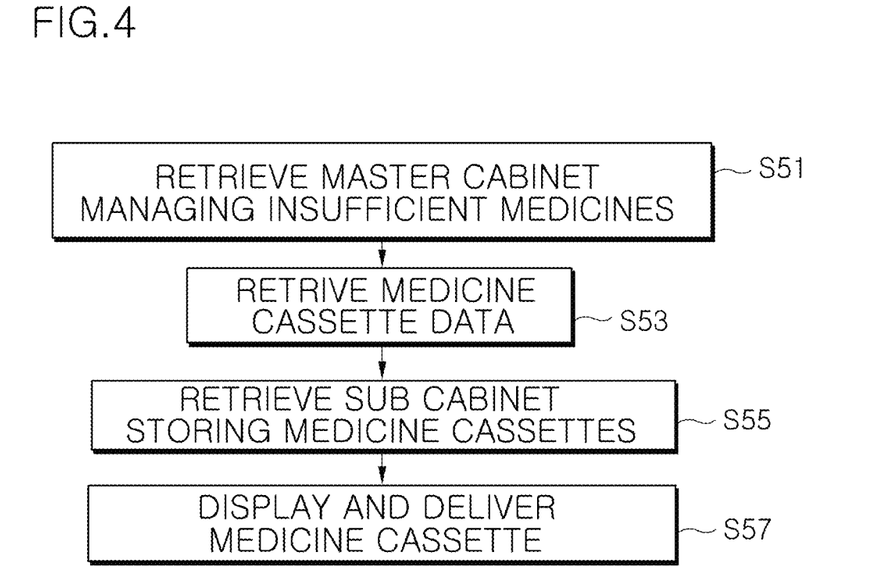
FIG. 4 is a detailed flow chart illustrating Step S50 of the dispensary management method according to the present invention.

Step S50 may be represented by a detailed flow chart as shown in FIG. 4.

First, a step of retrieving the master cabinet 70, which manages medicines, so as to retrieve the insufficient medicines is performed (S51).

Preferably, a step of storing information on medicine cassettes stored in the master cabinet 70 and the sub cabinet 80 in the database server is further provided before Step S51.

That is, a step of recognizing an identification code provided at each of the medicine cassettes and registering medicine information (medicine names, manufacturing companies, and the available periods) in advance is provided such that medicine retrieval can be rapidly performed based on the registered medicine information.

Subsequently, a step of retrieving information on the medicine cassettes, corresponding to the insufficient medicines, which are managed by the retrieved master cabinet 70 is performed (S53).

Figure 6:
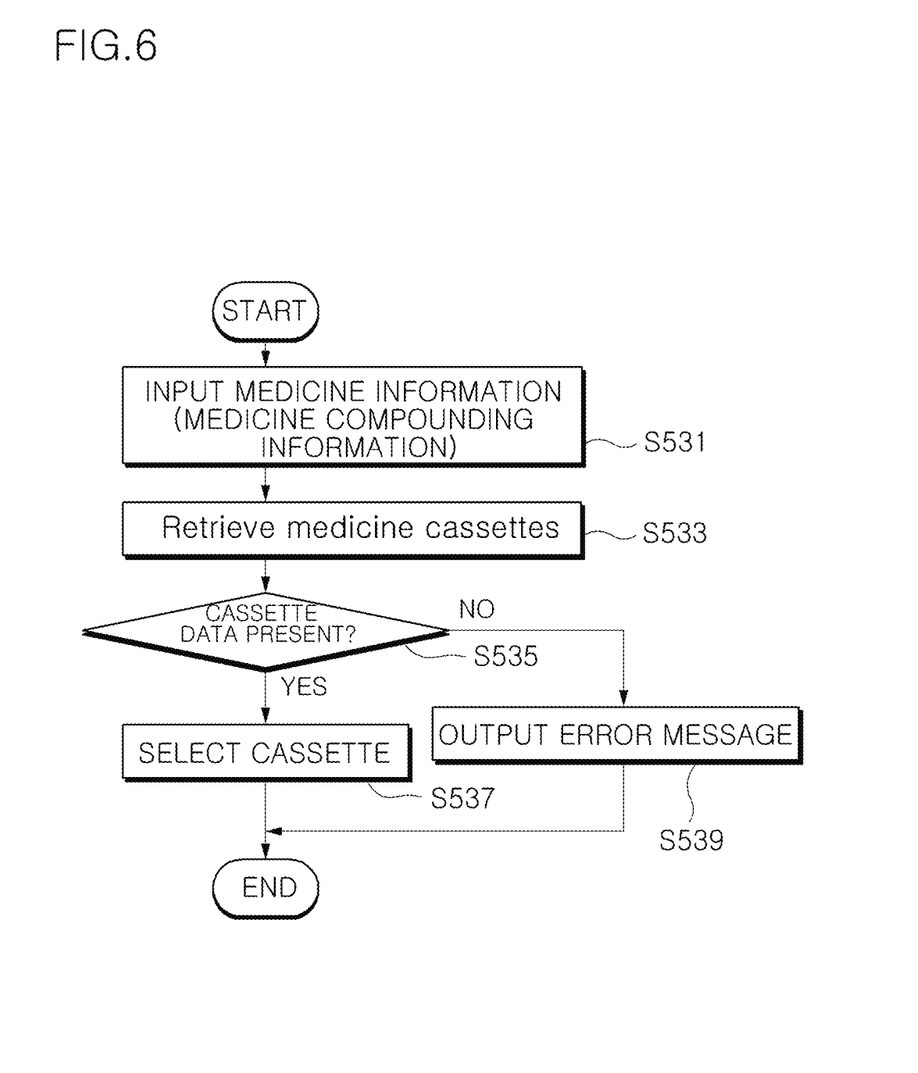
FIG. 6 is an overall flow chart illustrating the dispensary management method according to the present invention.

Step S53 may be represented by a detailed flow chart as shown in FIG. 6.

A step of inputting medicine information or medicine compounding information is performed (S531).

Preferably, a step of authenticating a user who retrieves the medicine cassettes is further provided before Step S531.

That is, it is possible to confirm information on a user who stores and delivers the medicine cassettes in and from the medicine cabinet, thereby improving efficiency in storage and management of medicines.

Subsequently, a step of retrieving the medicine cassettes is performed (S533), and then a step of determining whether medicine cassette data are present (S535).

At this time, if a plurality of pieces of the retrieved medicine cassette information is present as the result of the retrieval of the medicine cassettes, it is preferable to arrange the medicine cassettes in order of the medicine cassette information based on the available periods of the medicines.

Also, if a plurality of pieces of the retrieved medicine cassette information is present, it may be possible to arrange the medicine cassettes in order of information on the medicine cassette having the minimum movement distance based on the user retrieval position.

Figure 7:
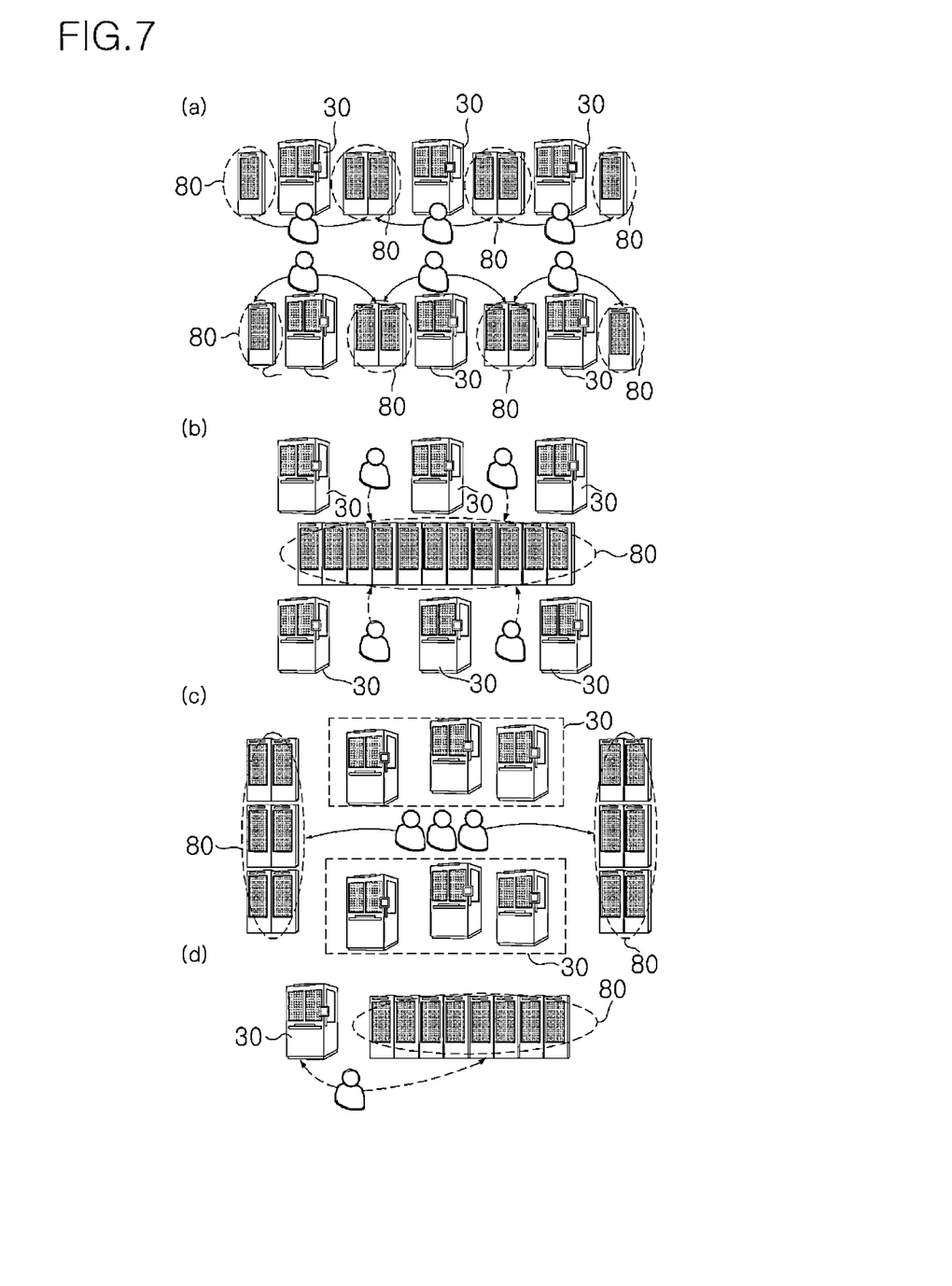
FIGS. 7A to 7D are views illustrating use embodiments of medicine storage cabinets based on a user position in the dispensary management method according to the present invention.

That is, FIGS. 7A to 7D are views illustrating the use of master cabinets 70 or sub cabinets 80 which are located at optimal positions based on the positions of automatic medicine compounding apparatuses 30 which are being retrieved by users. FIG. 7A illustrates an embodiment in which sub cabinets 80 located at the left and right sides of each of the automatic medicine compounding apparatuses 30 at which the users are present are used above all, and FIG. 7B illustrates an embodiment in which a group of sub cabinets 80 located among the automatic medicine compounding apparatuses 30 are used above all.

Also, 7C illustrates an embodiment in which groups of sub cabinets 80 located at the left and right sides of the automatic medicine compounding apparatuses 30 are used above all, and FIG. 7D illustrates an embodiment in which a group of sub cabinets 80 is used based on a automatic medicine compounding apparatus 30.

In this way, the present invention may be embodied in various forms based on the construction and scale of a dispensary.

It is possible to efficiently store and deliver a stock of the medicine cassettes through the arrangement sequence as described above.

If it is determined at Step S535 that the medicine cassette data are not present, a step of outputting a retrieval error message is performed (S539).

Subsequently, a step of selecting the optimum medicine cassette is performed (S537).

Subsequently, a step of retrieving a sub cabinet 80 storing the selected medicine cassette through the retrieved master cabinet 70 is performed (S55).

At Step S55, the master cabinet 70 may be retrieved since the master cabinet 70 also stores the medicine cassettes.

Subsequently, a step of informing the sub cabinet 80 of the insufficient medicine cassette and delivering a medicine cassette corresponding to the insufficient medicine cassette is performed (S57).

Subsequently, the delivered medicine cassette is stored in the automatic medicine compounding apparatus 30 to refill the insufficient medicines, and then a step of resetting the quantity of the medicines is performed (S60).

Figure 5:
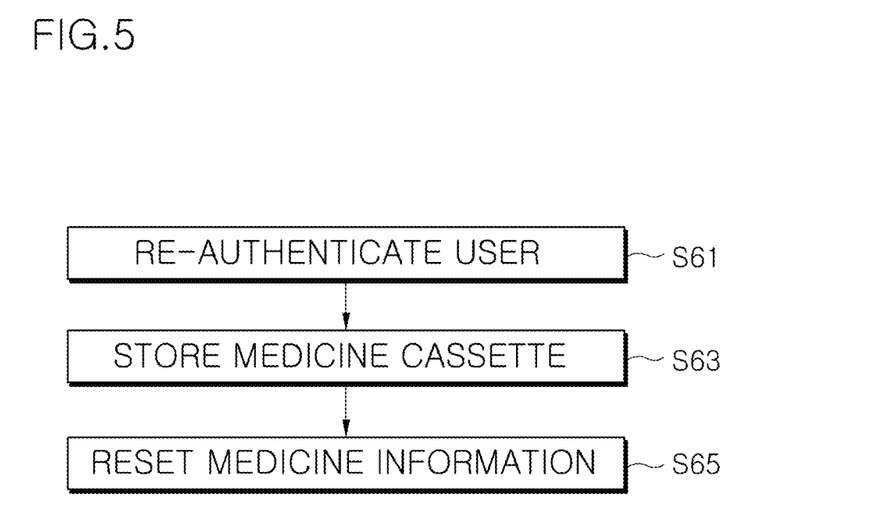
FIG. 5 is a detailed flow chart illustrating Step S60 of the dispensary management method according to the present invention.

Step S60 may be represented by a detailed flow chart as shown in FIG. 5.

First, a step of re-authenticating user information is performed (S61).

It is possible to easily confirm a person in charge who stores and delivers the medicine cassette in and from the automatic medicine compounding apparatus 30 through Step S61.

Subsequently, a step of storing the medicine cassette in the automatic medicine compounding apparatus 30 is performed (S63).

Subsequently, a step of resetting information on the medicines stored in the automatic medicine compounding apparatus 30 according to the storage of the insufficient medicine cassette is performed (S65).

It is possible to correctly confirm information on the medicines stored in the automatic medicine compounding apparatus 30 through Step S65.

Subsequently, a step of compounding the medicines is performed (S70).

Subsequently, a step of displaying a medicine compounding state and error information is performed (S80).

It is possible to determine whether the medicines which are being compounded coincide with the medicine compounding information and to confirm a current medicine compounding state and information on an error in the medicine compounding operation through Step S80.

Figure 11:
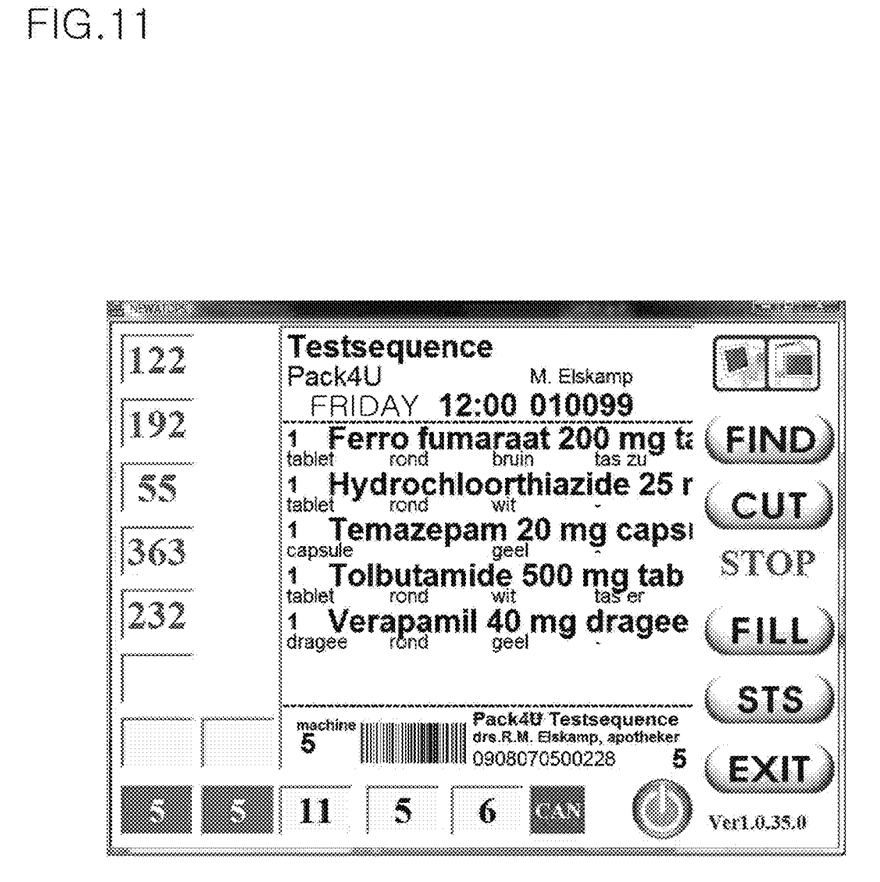
FIG. 11 is a view illustrating an embodiment of Step S70 of the dispensary management method according to the present invention.

FIG. 11 is a view illustrating an embodiment of Step S70. In this embodiment, it is possible to display information on a medicine compounding state of the automatic medicine compounding apparatus 30. Also, it is possible to display patient information, medicine compounding time information, compounded medicine information, the quantity of the medicines which are being compounded, the quantity of the medicines which have been compounded, the total number of doses of the medicines for a current patient, the complete number of doses of the medicines, etc.

Also, in the dispensary management method using the dispensary management system according to the present invention, it is preferable to schedule the retrieval sequence according to the order of priority upon simultaneous occurrence of a plurality of requests to retrieve medicines.

As is apparent from the above description, it is possible for the dispensary management method according to the present invention to retrieve information on cabinets storing medicine cassettes based on medicine information. Consequently, the present invention has the effect of rapidly retrieving storage positions of the medicine cassettes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A dispensary management method using a dispensary management system comprising a medicine compounding information server, a database server, a medicine compounding management unit, and a medicine storage management unit, the dispensary management method comprising:

inputting medicine compounding information to the medicine compounding information server;

determining whether medicines are insufficient based on the medicine compounding information using an automatic medicine compounding apparatus;

retrieving a cabinet storing medicines corresponding to the insufficient medicines using the database server upon determining that the medicines are insufficient;

resetting the quantity of the medicines upon filling of the automatic medicine compounding apparatus with medicines corresponding to the insufficient medicines;

compounding medicines using the automatic medicine compounding apparatus according to the medicine compounding information, authenticating a user who inputs the medicine compounding information, wherein the step of authenticating the user who inputs the medicine compounding information is performed before the step of inputting the medicine compounding information, displaying whether the automatic medicine compounding apparatus is normally operating in a standby mode, wherein the step of displaying whether the automatic medicine compounding apparatus is normally operating in the standby mode is performed before the step of authenticating the user who inputs the medicine compounding information, wherein the step of retrieving the master cabinet for managing the medicines corresponding to the insufficient medicines comprises:

inputting medicine compounding information or medicine information;

retrieving a medicine cassette corresponding to the medicine compounding information or medicine information; and selecting the retrieved medicine cassette, and wherein the step of retrieving the medicine cassette corresponding to the medicine compounding information or the medicine information comprises arranging the medicine cassettes in order of the medicine cassette information based on the available periods of the medicines upon determining that a plurality of pieces of the retrieved medicine cassette information is present.

2. The dispensary management method according to claim 1, wherein the step of retrieving the cabinet storing the medicines corresponding to the insufficient medicines using the database server comprises:

retrieving a master cabinet for managing medicines corresponding to the insufficient medicines;

retrieving a sub cabinet storing a selected medicine cassette;

displaying the storage position of the medicine cassette in the retrieved sub cabinet; and delivering the medicine cassette containing the medicines corresponding to the insufficient medicines.

3. The dispensary management method according to claim 1, further comprising authenticating a user who fills the medicine cassette upon filling of the medicines corresponding to the insufficient medicines, wherein the step of authenticating the user who fills the medicine cassette is performed before the step of resetting the quantity of the medicines.

4. The dispensary management method according to claim 1, wherein the step of compounding the medicines according to the medicine compounding information comprises displaying a medicine compounding state and error information.

5. The dispensary management method according to claim 1, further comprising recognizing an identification code provided at each of the medicine cassettes and registering medicine information (medicine names, manufacturing companies, and the available periods), wherein the step of recognizing the identification code provided at each of the medicine cassettes and registering medicine information is performed before the step of inputting the medicine compounding information or the medicine information.

6. The dispensary management method according to claim 1, further comprising authenticating a user who retrieves medicine cassettes, wherein the step of authenticating the user who retrieves the medicine cassettes is performed before the step of retrieving the medicine cassette.

7. The dispensary management method according to claim 1, wherein the step of retrieving the medicine cassette corresponding to the medicine compounding information or the medicine information comprises arranging the medicine cassettes in order of information on the medicine cassette having the minimum movement distance based on a user retrieval position upon determining that a plurality of pieces of the retrieved medicine cassette information is present.

\* \* \* \* \*